United States Patent
Rossi

(10) Patent No.: US 10,772,496 B2
(45) Date of Patent: Sep. 15, 2020

(54) METHOD FOR IMAGING RETINAL STRUCTURES

(71) Applicant: Ethan Andrew Rossi, Rochester, NY (US)

(72) Inventor: Ethan Andrew Rossi, Rochester, NY (US)

(73) Assignee: University of Rochester, Rochester, NY (US)

(*) Notice: Subject to any disclaimer, the term of this patent is extended or adjusted under 35 U.S.C. 154(b) by 412 days.

(21) Appl. No.: 15/564,676

(22) PCT Filed: Mar. 8, 2016

(86) PCT No.: PCT/US2016/021382
§ 371 (c)(1),
(2) Date: Oct. 5, 2017

(87) PCT Pub. No.: WO2016/164127
PCT Pub. Date: Oct. 13, 2016

(65) Prior Publication Data
US 2018/0064328 A1 Mar. 8, 2018

Related U.S. Application Data

(60) Provisional application No. 62/143,341, filed on Apr. 6, 2015.

(51) Int. Cl.
A61B 3/10 (2006.01)
A61B 3/14 (2006.01)
(Continued)

(52) U.S. Cl.
CPC .......... A61B 3/0025 (2013.01); A61B 3/1025 (2013.01); A61B 3/12 (2013.01);
(Continued)

(58) Field of Classification Search
CPC .......... A61B 3/103; A61B 3/14; A61B 3/113; A61B 3/1225; A61B 3/024; A61B 3/18; A61B 3/1015
(Continued)

(56) References Cited

U.S. PATENT DOCUMENTS 8,226,236 B2   7/2012  Williams et al.
2008/0007693 A1  1/2008  Williams et al.
(Continued)

FOREIGN PATENT DOCUMENTS

CN          101862178 A      10/2010

OTHER PUBLICATIONS

Toco Y. P. Chui et al.: "The use of forward scatter to improve retinal vascular imaging with an adaptive optics scanning laser ophthalmoscope," Biomedical Optics Express, vol. 3, No. 10, pp. 2537-2549 (2012) (13 pages).

(Continued)

Primary Examiner — Dawayne Pinkney
(74) Attorney, Agent, or Firm — Andrew J. Anderson, Esq.; Harter Secrest & Emery LLP

(57) ABSTRACT

A method for imaging retinal structures involves offsetting an imaging aperture from the center of the reflected/scattered light distribution. Images are obtained with the imaging aperture at multiple offsets with respect to the center. The various obtained images are co-registered to a reference confocal image in a reference wavelength and averaged to generate high signal to noise ratio images. The images may be combined in various ways to enhance the contrast of retinal structures that would not be visible in confocal images.

20 Claims, 1 Drawing Sheet

(51) Int. Cl.
*A61B 3/02* (2006.01)
*A61B 3/00* (2006.01)
*A61B 3/12* (2006.01)
*G02B 21/00* (2006.01)

(52) U.S. Cl.
CPC ..... *G02B 21/0028* (2013.01); *G02B 21/0064* (2013.01); *G02B 21/0024* (2013.01); *G02B 2207/129* (2013.01)

(58) Field of Classification Search
USPC ........ 351/205, 200, 206, 209–210, 221–222, 351/245–246
See application file for complete search history.

(56) References Cited

U.S. PATENT DOCUMENTS

| | | | |
|---|---|---|---|
| 2012/0300998 A1 | 11/2012 | Ioudovski et al. | |
| 2013/0208241 A1* | 8/2013 | Lawson | A61B 3/0091 351/206 |
| 2015/0070655 A1 | 3/2015 | Rossi | |

OTHER PUBLICATIONS

PCT/US2016/021382 International Search Report and Written Opinion of the International Searching Authority.

* cited by examiner

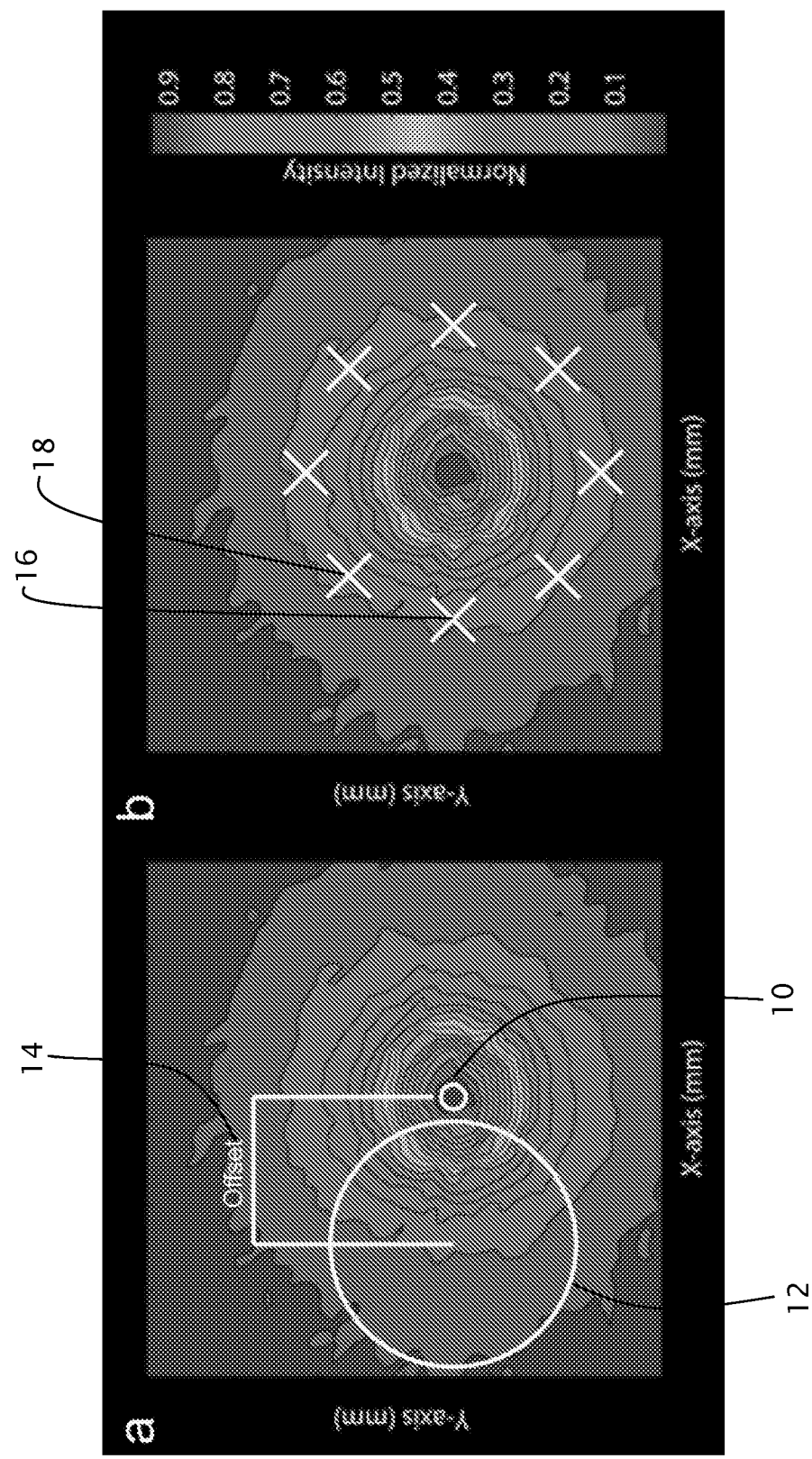

METHOD FOR IMAGING RETINAL STRUCTURES

STATEMENT REGARDING FEDERALLY SPONSORED RESEARCH OR DEVELOPMENT

This invention was made with Government support under Grant Nos. BRP EY014375, R01 EY021786, F32 EY021669 and P30 EY001319, awarded by the National Institutes of Health/National Eye Institute. The government has certain rights in the invention.

REFERENCE TO A "SEQUENCE LISTING"

Not applicable.

BACKGROUND

Non-invasive imaging of the retina and retinal structures of the living eye is important, especially for studying, diagnosing and monitoring diseases of the living human eye. Confocal imaging systems, including those using adaptive optics, have been employed to obtain images of various retinal structures. However, many retinal structures that are important for understanding the healthy and diseased retina are invisible using conventional confocal imaging methods. Phase imaging methods such as the one described here provide imaging of various retinal structures with better contrast than current methods and have the potential to reveal structures that are not accessible using current methods.

SUMMARY

According to aspects illustrated herein, there is provided a method comprising:

a. determining a center of three dimensional light distribution back scattered or reflected from the retina;

b. offsetting an imaging aperture from the center of light distribution such that the imaging aperture is located at a first offset position which is at a first angle and distance with respect to the center;

c. acquiring, at a first channel wavelength, a sequence of images at the first offset position, and acquiring simultaneously, at a reference channel wavelength, a sequence of reference images at a reference position;

d. repositioning the imaging aperture to a second offset position, the second offset position located at a second, different angle or distance with respect to the center than the first offset position;

e. acquiring, at the first channel wavelength, a sequence of images at the second offset position, and acquiring simultaneously, at a reference channel wavelength, a sequence of images at the reference position;

f. optionally repeating d. and e. for a desired number of additional offset positions located at different angles or distances from the center;

g. registering image sequences from the reference channel wavelength, and co-registering the image sequences obtained from each different offset position of the first channel wavelength using an identical reference frame from the reference channel image sequence; and h. averaging the co-registered image sequences from each offset position for the first channel wavelength to obtain a high signal to noise ratio image at each offset.

According to other aspects, the first channel wavelength may be the same or different from the reference channel wavelength. For example, the first channel wavelength and the reference channel wavelength may be different wavelengths in the visible light spectrum and/or the near infrared spectrum.

According to other aspects, the images from the offset positions may be combined to enhance contrast of the imaged retinal structures. Additionally, the registered reference channel wavelength images may be combined to obtain a composite reference channel wavelength image.

According to other aspects, all images of the first channel wavelength are acquired with a single detector, or without splitting light backscattered/reflected from the retina.

According to other aspects, the centering aperture is a circular aperture, such that light backscattered and/or reflected from a portion of the retina forms a three dimensional point spread function (or several theoretical point spread functions in the case of a broadband light source) at the focal plane where the aperture is placed. The imaging aperture may be offset from the center of the Airy disc by a distance of at least five Airy discs.

The methods disclosed herein permit reliable, non-invasive imaging of the living eye with improved contrast of various retinal structures. Retinal structures may include inner retinal structures such as blood vessel walls and nerve fiber bundles and outer retinal structures such as cone photoreceptor inner segments.

BRIEF DESCRIPTION OF THE DRAWINGS

FIG. 1 schematically illustrates the method according to various embodiments.

DETAILED DESCRIPTION

Initially, light backscattered and/or reflected from the retina is directed through an aperture 10, placed at the center of the focus of light from a light source of the imaging system. The light source may be provided by a scanning light imaging system, such as a scanning laser ophthalmoscope or a scanning laser microscope. When placed at the confocal position, the aperture 10 rejects light scattered from different out-of-focus layers of this portion of the retina. The shading in both sections of FIG. 1 schematically denotes the two-dimensional light intensity distribution around the focus of the imaging system, i.e., the shaded intensity distribution represents the point spread function, which can theoretically be described as an Airy disc. At the confocal position, the aperture 10 is at the center of the Airy disc.

As an example, aperture 10 may be a circular confocal aperture. This aperture may be relatively small, i.e., having a diameter not greater than ten times the size of the Airy disc, although other sizes are possible. For example, good results have been obtained employing a confocal aperture that is approximately nine times the size of the Airy disc.

Known methods may be employed to position the confocal aperture. Additionally, a method of automatically positioning the confocal aperture in the confocal position is described in commonly assigned US Publication No. 2015/0070655-A1, entitled "Apparatus and Method for Automatic Alignment in an Optical System and Applications", the disclosure of which is incorporated by reference in its entirety.

Alternately, the center of three dimensional light distribution back scattered or reflected from the retina can be determined by initially finding the center of light distribution on a model eye, and then offsetting the center when the actual eye to be imaged is placed in the system.

Imaging aperture 12 of the imaging system is initially located at first offset position 16. Generally, although not required, imaging aperture 12 may have a larger diameter than aperture 10.

Additionally, the center of imaging aperture 12 is offset by a desired amount from the center of the Airy disc, with offset 14 illustrated in FIG. 1. Typically, although not required, offset 14 will be greater than the radius of imaging aperture 12.

As examples, good images have been obtained employing offsets ranging from 6 to 16 Airy discs with an imaging aperture having a diameter of about 9 Airy discs.

Accordingly, first offset position 16 is located at a first angle and distance with respect to the center of light distribution, which as illustrated in FIG. 1, is the center of the Airy disc from aperture 10. The imaging system is employed to acquire, at a first channel wavelength, a sequence of first images at this first offset position 16. A suitable wavelength for the first channel is a wavelength in the visible light or near infrared spectrum, with 680 nm as an example.

The imaging system also acquires simultaneously, at a second channel wavelength (referred to hereinafter as the "reference" channel wavelength), a sequence of second images at a reference position (referred to hereinafter as the "reference" images). For the reference position, a fixed aperture at the confocal position of the imaging system may be employed. A suitable wavelength for the reference channel is a wavelength in the visible light or near infrared spectrum, with 796 nm as an example. However, the first and reference wavelengths may be the same or different, and other wavelengths may be employed so long as the eye may be safely exposed to the wavelength for the duration necessary for acquiring image sequences.

The center of imaging aperture 12 is relocated to second offset position 18, located at a different angle or distance with respect to the center of light distribution, which as illustrated in FIG. 1 is the center of the Airy disc. A sequence of first images is similarly obtained at this second offset position at the first channel wavelength, and simultaneously, a sequence of reference images is obtained at the reference position for the reference channel wavelength.

Imaging aperture 12 may be relocated to other offset positions, as schematically illustrated in FIG. 1, with sequences of first images obtained at each offset position for the first channel wavelength, and with sequences of reference images obtained simultaneously at the reference position for the reference channel wavelength. FIG. 1 illustrates four sets of offset positions, with each set varying by 180 degrees and at the same distance from the center, although other arrangements of the offset positions are possible. For example, the various offset positions do not need to be at the same distance from the center, and the various offset positions do not need to vary by 180 degrees.

The acquired first images and reference images at each offset position are registered.

In order to more reliably obtain high contrast, the sequences of first and reference images are acquired for each offset position, with all first images co-registered to the reference wavelength image using a common image reference frame. This provides data from a representative sample of angles about the Airy disc, allowing the contrast of various retinal structures with different scattering/reflectivity properties to be enhanced and allowing one to compensate for aberrant individual images. As an example, if an individual image does not meet a pre-determined threshold value for image quality, such individual image may be disregarded. In any event, in obtaining a sequence of images for each offset position, the retained images at a given offset position are co-registered and averaged.

A further benefit of obtaining images at different offset positions is that it provides flexibility to obtain and examine contrast enhancement of particular retinal structures that may have asymmetric scattering profiles. For example, blood vessel walls are best visualized when the aperture positions are at orthogonal angles to the vessel path.

Accordingly, the co-registered image sequences from each offset position for the first channel wavelength are averaged to obtain a high signal to noise ratio image at each offset position. These co-registered images may be combined in a manner to enhance contrast of any specific retinal structures of interest. These images from the offset positions may be combined in known manners, such as subtracting, adding, or dividing the images. For example, in the illustrated embodiment where there are four sets of offset positions, each varying by 180 degrees, one may take difference of the images obtained at angles separated by 180 degrees and divide by their sum.

As mentioned, image sequences are obtained at both the first and reference channel wavelengths simultaneously. These image sequences are acquired simultaneously to allow co-registration. This is a key benefit of the reference wavelength image as it can be used as an unchanging reference to allow each first wavelength offset position image sequence to be co-registered to an identical reference frame obtained in the reference channel. Co-registration allows eye motion that occurred during imaging to be removed, undistorting the images and placing them in register for averaging. A method employing co-registration of fluorescent images to adjust for eye motion during image capture is described in U.S. Pat. No. 8,226,236 (Williams et al.), the disclosure of which is incorporated by reference in its entirety.

Another benefit of acquiring images for at least two channel wavelengths is that some retinal structures may have better resolution and contrast at the first channel wavelength, whereas better quality images of other retinal structures may be obtained at the reference channel wavelength. Accordingly, the registered reference channel wavelength image sequences may be combined to obtain a composite reference channel wavelength image in order to view any such other retinal structures.

Additionally, if desired, images from the offset positions may be combined with the composite reference channel image. For example, an image from an offset position may be overlaid with the composite reference image to highlight certain retinal structures or to identify any artifacts from the imaging process.

The methods are useful for various imaging systems, especially confocal scanned imaging systems including a scanning laser ophthalmoscope or a scanning laser microscope. Quality images have been obtained in the living eye of outer retinal structures such as cone photoreceptor inner segments, and inner retinal structures such as blood vessel walls employing an adaptive optics scanning laser ophthalmoscope.

A further benefit of this method is that all images of the first channel wavelength may be acquired with a single detector, and without splitting light directed on the retina. Therefore, it does not require more than one detector in addition to the confocal imaging system, and does not require any additional optical elements to "split" light such as required for various "split detection" imaging techniques. Generally, however, the use of a single detector and no light splitting for the first images will involve the first and reference wavelengths being different.

The aspect where the first and reference channel wavelengths are the same would be similar to split detection in that the confocal light is split off to a first detector and the remainder of the light is sent to the second detector. However, even for this aspect, two detectors would be employed to capture the first images, which is still less than three detectors required of prior systems.

If desired, the imaging aperture may be positioned at a desired tilt angle with respect to the plane in which the retina is located. In the illustrated embodiment, the imaging aperture is not tilted, but this aperture may have a tilt angle greater than zero.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

The invention claimed is:

1. A method for imaging retinal structures, comprising:
   a. determining a center of three dimensional light distribution back scattered or reflected from the retina;
   b. offsetting an imaging aperture from the center of light distribution such that the imaging aperture is located at a first offset position which is at a first angle and distance with respect to the center;
   c. acquiring, at a first channel wavelength, a sequence of images at the first offset position, and acquiring simultaneously, at a reference channel wavelength, a sequence of reference images at a reference position;
   d. repositioning the imaging aperture to a second offset position, the second offset position located at a second, different angle or distance with respect to the center than the first offset position;
   e. acquiring, at the first channel wavelength, a sequence of images at the second offset position, and acquiring simultaneously, at a reference channel wavelength, a sequence of images at the reference position;
   f. optionally repeating d. and e. for a desired number of additional offset positions located at different angles or distances from the center;
   g. registering image sequences from the reference channel wavelength, and co-registering the image sequences obtained from each different offset position of the first channel wavelength using an identical reference frame from the reference channel image sequence; and
   h. averaging the co-registered image sequences from each offset position for the first channel wavelength to obtain a high signal to noise ratio image at each offset position.

2. The method of claim 1, further comprising combining the images from the offset positions to enhance contrast of imaged retinal structures.

3. The method of claim 2, wherein combining the images from the offset positions includes at least one of subtracting, adding and dividing said images.

4. The method of claim 1, further comprising combining the registered reference channel wavelength image sequences to obtain a composite reference channel wavelength image.

5. The method of claim 1, further comprising combining the images from various offset positions with the composite reference channel wavelength image.

6. The method of claim 1, wherein the first channel wavelength is the same or different from the reference channel wavelength.

7. The method of claim 6, wherein the first channel wavelength is in the visible light spectrum and the reference channel wavelength is in the near infrared spectrum.

8. The method of claim 6, wherein the first channel wavelength is in the near infrared spectrum and the reference channel wavelength is in the visible light spectrum.

9. The method of claim 1, wherein light back scattered or reflected from the retina is directed through an aperture placed at a center of the focus of light from a light source to determine the center of three dimensional light distribution.

10. The method of claim 1, wherein all images of the first channel wavelength are acquired with a single detector.

11. The method of claim 10, wherein all images of the first channel wavelength are acquired without splitting light directed on the retina.

12. The method of claim 1, further comprising acquiring the images with a confocal imaging system including a scanning laser ophthalmoscope or a scanning laser microscope.

13. The method of claim 11, wherein the confocal imaging system includes an adaptive optics scanning laser ophthalmoscope.

14. The method of claim 1, wherein the imaging aperture is offset from the center of the Airy disc by a distance of at least five Airy discs.

15. The method of claim 1, wherein the imaging aperture is positioned at a desired tilt angle with respect to a plane in which the retina is located.

16. The method of claim 15, wherein the tilt angle is zero.

17. The method of claim 15, wherein the tilt angle is greater than zero.

18. The method of claim 1, comprising acquiring images of inner retinal structures.

19. The method of claim 18, wherein the inner retinal structures include blood vessel walls.

20. The method of claim 1, comprising acquiring images of cone photoreceptor inner segments.

* * * * *